(12) United States Patent
Vovan et al.

(10) Patent No.: US 8,239,215 B2
(45) Date of Patent: Aug. 7, 2012

(54) APPARATUS AND METHOD FOR REVENUE DISTRIBUTION GENERATED FROM DELIVERING HEALTHCARE ADVERTISEMENTS VIA EMR SYSTEMS, RHIN, AND ELECTRONIC ADVERTISING SERVERS

(75) Inventors: Andre T. Vovan, Irvine, CA (US); Chris T. Vovan, Irvine, CA (US); William Allen Mincey, Irvine, CA (US); David Howard Glazov, Palo Alto, CA (US)

(73) Assignee: Mitochon Systems, Inc., Newport Beach, CA (US)

(*) Notice: Subject to any disclaimer, the term of this patent is extended or adjusted under 35 U.S.C. 154(b) by 944 days.

(21) Appl. No.: 12/015,703

(22) Filed: Jan. 17, 2008

(65) Prior Publication Data

US 2008/0172252 A1  Jul. 17, 2008

Related U.S. Application Data

(60) Provisional application No. 60/885,375, filed on Jan. 17, 2007.

(51) Int. Cl.
*G06Q 10/00* (2012.01)
*G06Q 50/00* (2012.01)

(52) U.S. Cl. ............................................. 705/2; 705/3
(58) Field of Classification Search .................. 705/2–3
See application file for complete search history.

(56) References Cited

U.S. PATENT DOCUMENTS

| | | | | |
|---|---|---|---|---|
| 6,820,058 | B2* | 11/2004 | Wood et al. | 705/4 |
| 7,246,070 | B2* | 7/2007 | Schwartz et al. | 705/4 |
| 2001/0032124 | A1* | 10/2001 | Savage et al. | 705/14 |
| 2004/0260577 | A1* | 12/2004 | Dahlin et al. | 705/2 |
| 2006/0080146 | A1* | 4/2006 | Cook et al. | 705/2 |
| 2006/0190296 | A1* | 8/2006 | Hackett et al. | 705/2 |
| 2006/0277075 | A1* | 12/2006 | Salwan | 705/3 |
| 2008/0021739 | A1* | 1/2008 | Brock | 705/3 |

OTHER PUBLICATIONS

Citinka, Helen, Healthcare Utilization under Monitoring and Capitation, Dissertations Abstract International, vol. 6309A, p. 3268, 141 Pages.*

* cited by examiner

*Primary Examiner* — Jason Dunham
*Assistant Examiner* — Amber Altschul
(74) *Attorney, Agent, or Firm* — Blue Capital Law Firm, P.C.

(57) ABSTRACT

A system and method for effectively distributing revenues generated from delivering specific healthcare advertisements and non health-care specific advertisements over electronic medical record systems (EMR) and a regional healthcare information network (RHIN) using an electronic advertising server in a manner compliant with HIPAA and Federal Anti-Kickback laws. The system consists of several components including: (1) an internet or intranet based patient portal used by health consumers to communicate with their health care provider; (2) a protocol at the patient portal in which the health consumer may choose from a menu of possible actions; 3) an ad server providing appropriate protocol to distribute the advertisement on the patient portal and EMR; 4) an EMR system used by a physician to record the clinical encounters with the healthcare consumer; 5) a RHIN which bridges the EMR systems and patient portals to create a healthcare network or community of physicians, healthcare consumers and other providers using this system; and 6) an advertisement targeting process.

19 Claims, 8 Drawing Sheets

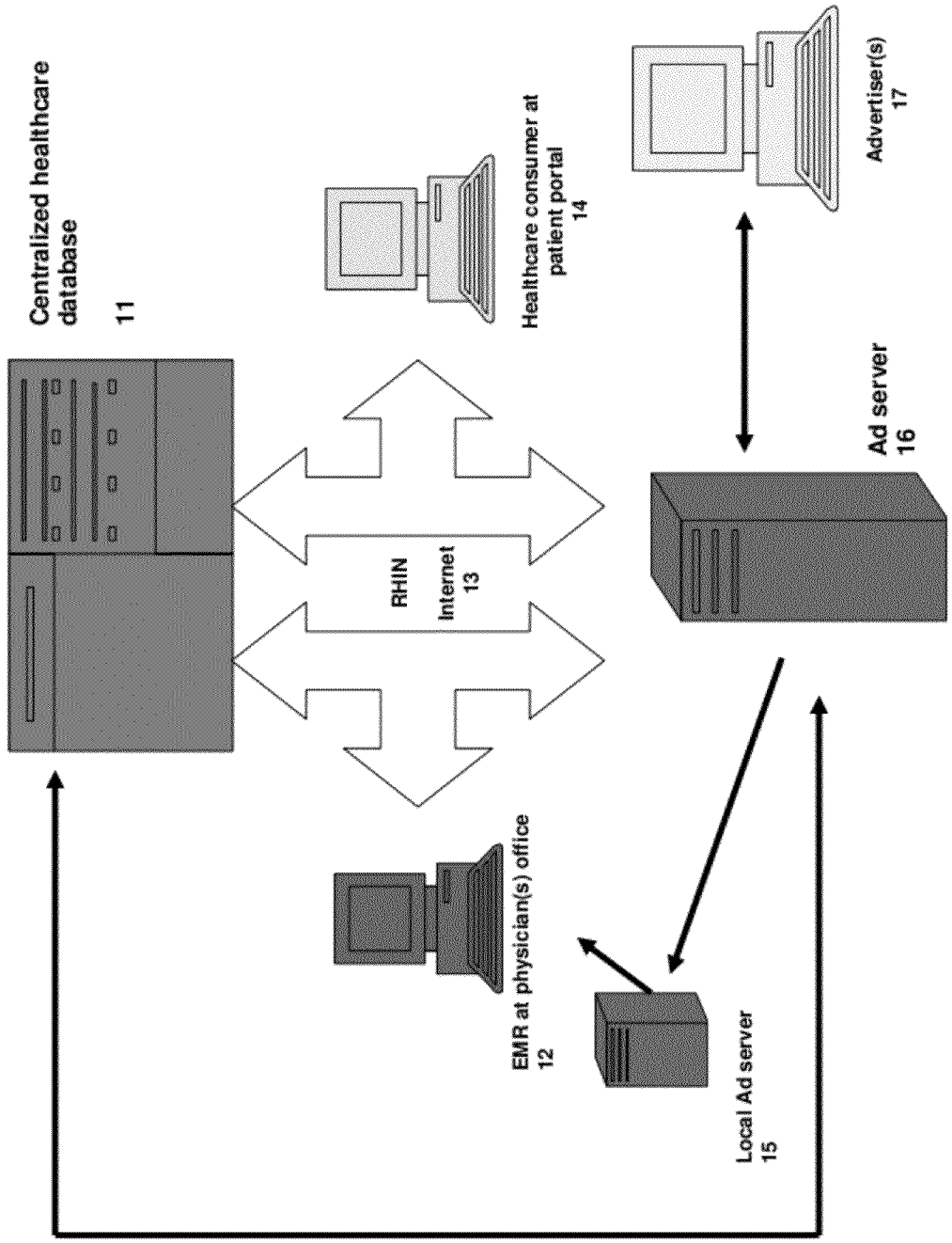

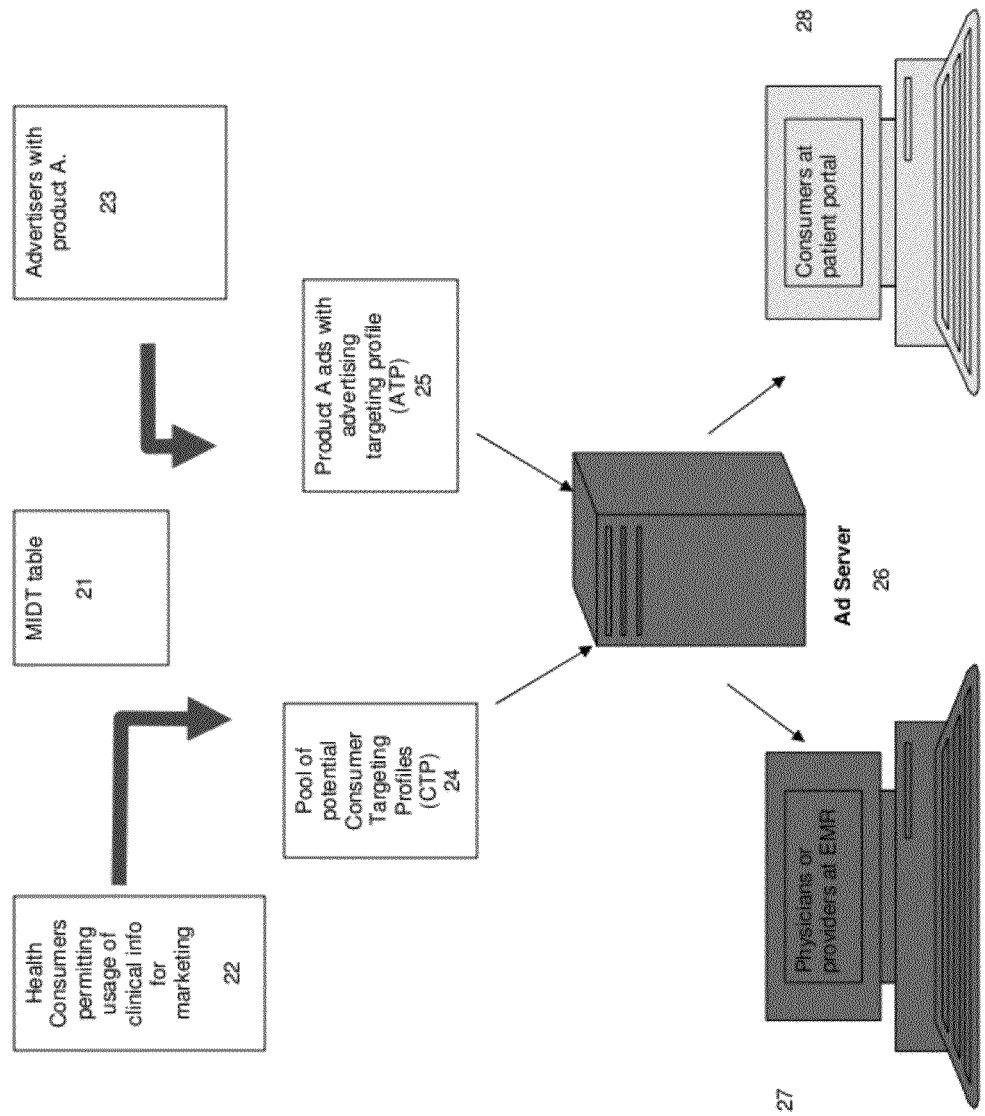

FIG. 3

Medication Illness Disease Table (MIDT)

| Name (generic name) | DC number (hypothetical) | Drug classification | Indicated treatment (ICD-9 code) | Complementary treatment or products (DC) | Competitor or substitute products or treatments and DC (hypothetical) | Risk factors and associated illness/ condition and the corresponding ICD 9 or ICD 10 |
|---|---|---|---|---|---|---|
| Plavix (clopidogrel) | m105 | Antiplatelet | Stroke (434) | Aspirin (m005), Coumadin (m010), anti cholesterol drugs (m115), smoking cessation (s200), exercise (s304) | Ticlid (Ticlopidine) m106 | Atrial fibrillation (427), smoking (305.1), hyperlipidemia (272), diabetes (250), hypertension (401) |
| Lipitor | m207 | Antilipid | Coronary artery disease (414), stroke (434) | Aspirin (005), antihypertension drug (408), smoking cessation (200), exercise (304) Insulin (111) | Zocor (simvastatin) m208 | Obesity (278) smoking (305.1), hyperlipidemia (272), diabetes (250), hypertension (401) |

Columns labeled 31, 32, 33, 34, 35, 36, 37.

Assigning Consumer Target Profile (CTP)

FIG. 7: Permissive advertisement process

Revenue distribution model

APPARATUS AND METHOD FOR REVENUE DISTRIBUTION GENERATED FROM DELIVERING HEALTHCARE ADVERTISEMENTS VIA EMR SYSTEMS, RHIN, AND ELECTRONIC ADVERTISING SERVERS

CROSS REFERENCES TO RELATED APPLICATIONS

This application claims the benefit of Provisional Application Ser. No. 60/885,375, filed on Jan. 17, 2007, which is herein incorporated by reference.

BACKGROUND OF THE INVENTION

1. Technical Field

The present invention relates to healthcare advertisements, and more specifically to an apparatus and method for effectively distributing revenues generated from delivering specific healthcare and non-healthcare advertisements over electronic medical record systems (EMR) and a regional healthcare information network (RHIN) using an electronic advertising server.

2. State of the Art

The current healthcare system is costly and inefficient. Adoption of electronic medical record systems is generally accepted as a means to increase efficiency, decrease duplication and decrease costs in healthcare delivery. A regional health information network is a collection of interconnected EMR systems that improves communication and transaction between healthcare providers (hospitals, physicians, etc.) and consumers. The current business model to sell EMR systems to physicians or other healthcare providers is based on the return on investment model. The overall cost of the EMR system is recouped by increased efficiency and effectiveness of the physician's practice using the EMR system over a period of time. A typical EMR business model consists of licensing the EMR software with or without hardware at an upfront cost and/or charging a yearly fee for software upgrades, maintenance and services. Additional services such as billing and proactive management are also often offered. All revenue streams are derived from licensing the software and providing services to the purchasing physicians. These EMR systems are prohibitively costly for physician and are the biggest barrier of EMR adoption by the healthcare industry.

Furthermore, healthcare advertisement often does not reach the target audience because HIPAA laws forbid the usage of protected personal health information from being used for marketing without the direct informed consent of the consumer party. Interested advertising parties usually seek to deliver their advertisement to a specific audience. For example, drug manufacturers of diabetic medication would wish to target patients who have diabetes as well as the health care providers treating these patients. Furthermore, it is well known that there are certain diseases that are statistically related to each other because of a causative effect, a similar underlying pathology or other biological reasons. For instance, people with diabetes may also develop vascular disease, heart disease, obesity, kidney disease, and/or chronic pain. Therefore, companies that market medications treating heart disease or obesity would benefit from targeting these diabetic patients and the healthcare providers caring for these diabetic patients and potentially prescribing these medications as well.

The current EMR model is not only costly to physicians and other healthcare providers but also does not provide an effective means to allow physicians and consumers to receive information and advertisements on drugs that are specific to the health condition in a manner that protects the patients privacy compliant with HIPAA laws.

Accordingly, what is needed is a system and method for overcoming the foregoing deficiencies, and ensuring that consumers and physicians receive the appropriate healthcare information and advertisements on medication, medical device and healthcare services that are specific to their illness and/or treatment.

SUMMARY OF THE INVENTION

The present invention broadly provides a system and method to effectively deliver specific healthcare advertisements over electronic medical record systems (EMR) and a regional healthcare information network (RHIN) using an electronic advertising server. The present system consists of several components including: (1) an internet or intranet based patient portal used by health consumers to communicate with their health care provider; (2) a protocol at the patient portal in which the health consumer may (a) grant consent for the usage of his/her de-identified health record for marketing or commercial purposes, (b) choose from a menu of possible advertisement categories to be generated or (c) choose to receive non-specific advertisements; (3) a protocol to de-identify the patients' health records and to encode the allowed health information for targeting by advertisers; (4) an ad server using one of the choices selected in step 2 to provide the appropriate protocol to distribute the advertisement on the patient portal; (5) an EMR system used by a physician to record the clinical and financial encounters with the healthcare consumer; (6) an ad server which distributes the appropriate advertisement on the EMR to the physician based on the physician's demographic data and/or clinical data of the healthcare consumer if consent is given by that healthcare consumer; (7) a RHIN which bridges the EMR systems and patient portals to create a healthcare network or community of physicians, healthcare consumers and other providers using this system; (8) a private secure access point for other healthcare providers; and (9) an advertisement targeting process in which advertisers will be allowed to choose from a menu of target driven choices to select the targeted consenting audience without revealing their protected personal health information.

Protected Health Information (PHI) is individually identifiable information (information that relates to the past or present health of an individual) that includes the following fields: names; geographic subdivisions smaller than a state, including street address, city, county, precinct, zip code, and their equivalent geocodes; dates directly related to an individual, including birth date, admission date, discharge date, date of death; telephone numbers; fax numbers; electronic mail addresses; social security numbers; medical record numbers; health plan beneficiary numbers; account numbers; certificate and/or license numbers; vehicle identifiers and serial numbers, including license plate numbers; device identifiers and serial numbers; Web Universal Resource Locators (URLs); Internet Protocol (IP) address numbers; biometric identifiers, including finger and voice prints; full face photographic images and any comparable images; and any other unique identifying number, characteristic, or code. Removal of these fields creates a presumption that the information is de-identified and thus no longer subject to the Privacy Regulation.

The above choices include targeting an audience currently using the services or product being advertised, an audience using substitute or complementary products or services being advertised, an audience with health conditions which increase their current or future risks for any health condition that may require the services or product being advertised. Using this information, a protocol will match the targeted audience with the available matching de-identified health consumers. The ad server then distributes the appropriate ad(s) to the health consumers using the patient portal and to the physician or other health provider using the EMR system.

The present invention allows two distinct embodiments not found in existing models. The first embodiment is a direct-to-consumer channel in which healthcare related advertisements can be specifically targeted to consumers by using their clinical information. This channel allows advertisers to specifically target consumers based on what medication they use, what illnesses they have, and what risk factors they have for developing an illness or condition by which the products are approved to treat. Advertisers can also target consumers based on their usage of a competitor's product or a complementary product or services. This is done in a manner that is consistent with current HIPAA laws in which the targeted audience consents to receiving the marketing media and the targeted audience's personal identifying data (name, social security number, address, birthdates, etc.) are not used.

The network also allows for a direct-to-physician channel in which advertisers can reach physicians treating healthcare consumers because healthcare consumer clinical data can be used for marketing purposes if consent is given by the consumer. If consent is not given by the consumer, then the physician will receive advertising based on his choice and/or his demographic information such as his medical specialty.

The present invention also allows healthcare providers to benefit from the revenues generated from non-healthcare advertising on the EMR systems. Revenue from healthcare advertisements of products or services covered by the federal or state healthcare programs cannot go to the physicians or healthcare providers using the EMR or the regional healthcare network due to anti-kickback laws. However, advertisement revenues from product or services that are not covered by federal or state healthcare programs can be shared with the healthcare provider using the electronic medical record, therefore, allowing physicians to benefit from these revenues.

BRIEF DESCRIPTION OF THE DRAWINGS

Various features of this system and method, which are believed to be novel, are set forth with particularity in the appended claims. The present method may best be understood by reference to the following description, taken in connection with the accompanying drawings:

FIG. 1 is a diagram illustrating the advertising network over RHIN

FIG. 2 describes the process of encoding a patient's health record and an advertisement using the codes on the MIDT table.

FIG. 3 illustrates an MIDT table.

DETAILED DESCRIPTION OF THE DRAWINGS

Figure 4:
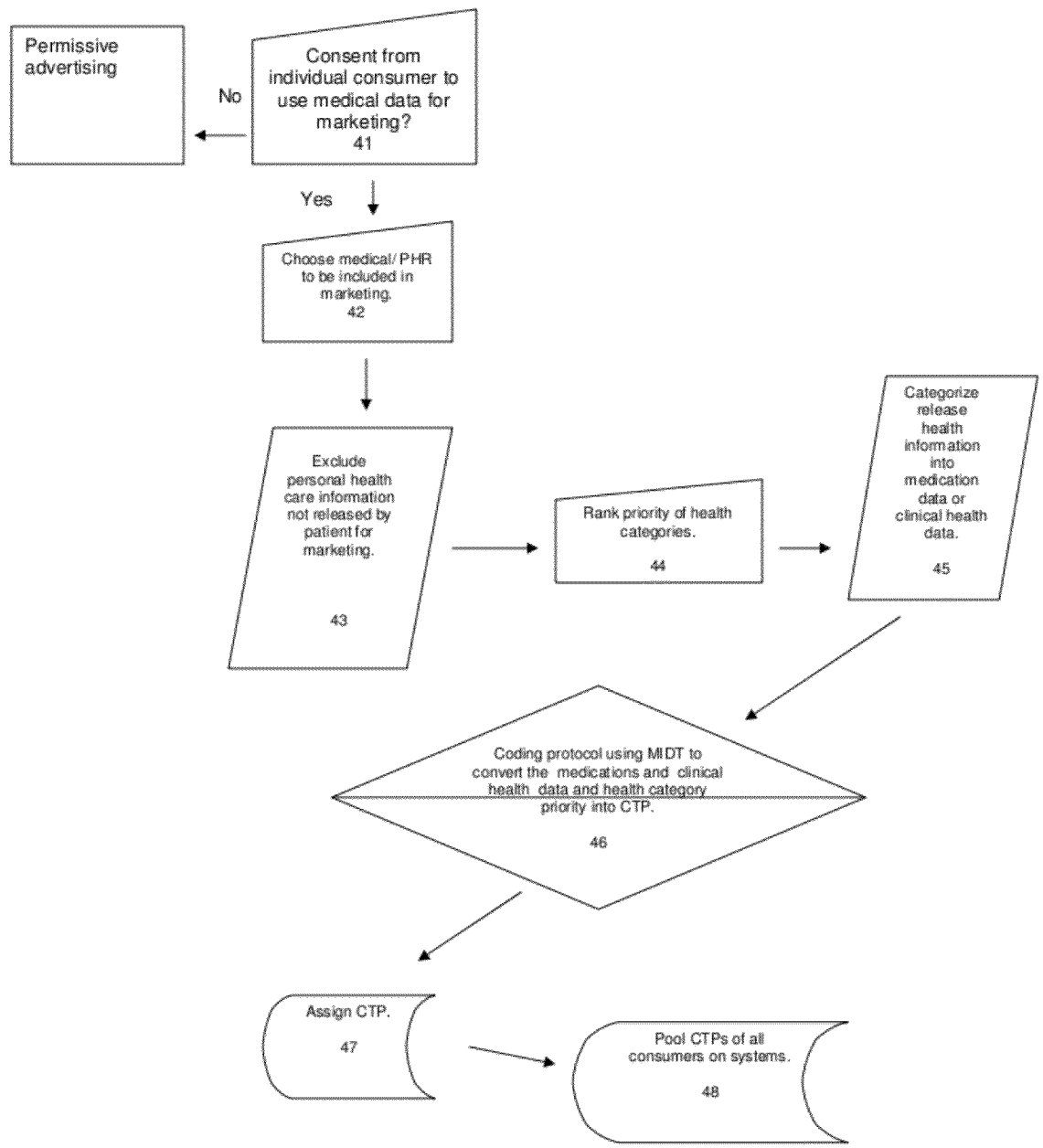
FIG. 4 illustrates how a CTP is generated.

The following detailed description is of the best presently contemplated mode of carrying out the present invention. This description is not to be taken in a limiting sense, but is made merely for the purpose of illustrating general principles of embodiments of the present invention. The scope of the present invention is best defined by the appended claims.

The present invention provides an apparatus and method for effectively delivering specific healthcare advertisements over electronic medical record systems (EMR) and a regional healthcare information network (RHIN) using an electronic advertising server.

FIG. 1 describes the general relationship between the Centralized healthcare data bass 11, the EMR system 12, the regional healthcare information network 13, and the central ad server 16, and the patient portal 14. The centralized healthcare database 11 hold general medical clinical information collected from both the electronic medical record 12 and the healthcare consumer patient portal 14. The centralized healthcare database 11 interacts with the EMR 12 and the healthcare consumer patient portal 14 via a secured regional healthcare information network (RHIN) internet linkage 13.

The EMR system 12 at the physician's office is an electronic medical records systems housing clinical data of individual healthcare consumers. This information can exist via a local software application at the healthcare service site or can be hosted by an application service provider. The software of the EMR 12 captures relevant clinical encounter data between the healthcare consumers and the treating physicians or other healthcare providers. The EMR 12 application is used by physicians and other healthcare providers to document the patient's conditions and progressions of their treatment and capture and bill consumers for the services rendered. The EMR 12 essentially replaces the paper charts and allows physicians electronic access to the patient's disease courses. It also allows the physicians on the RHIN network 13 to electronically communicate with other physicians, payers, other healthcare facilities as well as health insurers on the network. The ERM 12 is essentially the physician's portal into the present regional healthcare information network (RHIN 13). The information that is entered into the physician's EMR systems 12 can be held locally at a local healthcare database, replicated, or held centrally at a centralized healthcare database 11.

The patient portal 14 in the system is an internet website portal allowing healthcare consumers to communicate with their treating physicians. At the patient portal 14 healthcare consumers may view their personal healthcare records. Patients may also choose to perform various functions including receiving notifications from their physician's office as well as request medications, refills, and/or schedule doctor's appointments. The patients also can attain or search for healthcare information at this web portal 14. Information entered into the patient portal 14 is stored at the centralized healthcare database 11 and is shared with the physicians at his EMR system 12. The component that allows patients and physicians to communicate to each other is the regional healthcare information network 13 (a secured internet linkage protocol).

The regional healthcare information network 13 is an application which connects the EMR system 12 via a secure standard electronic communication protocol. The RHIN 13 is that act as a bridge between the EMR systems 12 and the patient portal 14.

The central ad server 16 is a an electronic system that uses the clinical information stored in the centralized healthcare database 11 or local database and the healthcare information of the healthcare consumer as a reference to deliver appropriate advertisements to consumers and healthcare providers. The central ad server 16 directs specific advertisements to the healthcare consumers at the patient portal 14 and to physicians at the EMR office 12. The central ad server 16 may deliver advertisements to the physicians directly to the EMR office 12 from the centralized location, or the central ad server 16 may send the advertisements to a local ad server 15 located at the physicians' office or other healthcare providers facilities. The local ad server 15 will then deliver the advertisement to the user of the EMR 12. The central ad server 16 acts as a distributor for the advertisers who wish to distribute their advertisements to healthcare consumers and providers. Advertisers may load their advertisements onto the central ad servers 16 and designate where they wish those advertisements to be delivered.

FIG. 2 describes the process of encoding a patient's health record and an advertisement using the codes on the MIDT table. Healthcare consumers at the patient portal first grants permission for the use their clinical data (which includes their medication profile as well as their disease profile) to be used for marketing purposes 22. The consumers' medication and illness information is then encoded using a Medication, Illness, and Disease Table (MIDT) 21 which holds the codes for different medications and illnesses and how hey are related to each other. The codes are used to generate a consumer targeting profile (CTP) 24 for each consenting consumer. The CTP 24 is a numeric representation of the consumer's medical information.

Advertisers 23 then use the information on MIDT table 21 to assign an advertising targeting profile (ATP) 25 to each advertisement. The ATP 25 is a numeric representation of the information contained in such advertisement.

The CTPs 24 and ATPs 25 are sent to the central ad server 26 where they are matched. The central ad server 26 then sends the appropriate advertisements to consumers at the patient portal 28 and their treating physicians at the EMR office 27 based on these CTP and ATP matches.

FIG. 3 displays the Medication, Illness and Disease Table (MIDT) in detail. The Medication, Illness and Disease Table puts different types of medications, illnesses, and diseases into categories based upon several factors including classifications and indicated treatment of the each medication, direct competitors or substitute products, risk factors, and associated illnesses that may increase by using such medications.

The first column 31 contains the name and the generic name of the drug or medical device, e.g., Plavix and Lipitor. The second column 32 is the corresponding drug or device code. For instance, the hypothetical device codes, m105 and m207, may represent Plavix and Lipitor, respectively. The device coding system 32 can be based on the national drug code (NDC) or any drug coding system. The third column 33 contains the drug classification or device classification. For example, Plavix, is classified as an antiplatelet drug and Lipitor is an anti-lipid drug. The fourth column 34 describes the disease the drug is approved to treat. Each disease is represented by the International Classification of Disease 9th iteration code (ICD-9) or any later iterations. However, other disease coding systems may also be used including SNOMED.

The fifth column 35 describes the complementary treatment or product which are often used to co-treat the illness that the medication is used. Complementary treatment or product are not direct competitors of the medication in question but are generally used to co-treat the same illness. For instance, complementary treatment and product such as aspirin, coumadin, cholesterol medications, smoking cessation services, as well as exercise, are recommended to be used with Plavix to co-treat stroke. Therefore, manufacturers of Plavix and Aspirin can target patients with stroke in marketing their products.

The sixth column 36 lists the competitor or substitute product or treatment for the medication in question. For instance, the medication Ticlid which is approved to treat strokes, is a direct competitor of Plavix. This information allows advertisers to target not only consumers who use their products but also consumers who use their competitors' products. The last column 37 identifies the risk factors or associated illnesses of the drug or product in question. For example, the conditions of atrial fibrillation, smoking, hyperlipidemia, diabetes, hypertension can increase the likelihood of strokes, the condition which can be treated using Plavix. Therefore, advertisers can target potential audience who are at risk of having certain health conditions which predisposed them to using the product or treatment in question.

FIG. 4 illustrates the process of how a consumer targeting profile is created after health consumer consents to have his/her clinical data be used for marketing. The healthcare consumer at the patient portal is first prompted to give consent 41 to have his clinical information be used for advertising. If the consumer gives consent, the consumer is then prompted to choose which aspect of his/her private health records may be used for marketing 42. The consumer may have his entire medical records or only a certain portion of his medical records be released for marketing. Any patient information or health conditions not released will be excluded 43. The consumer's personal identifying information as required by HIPAA Law to be deemed de-identified will also be excluded (i.e., name, social security number, address) 43.

The system then asks the consumer to rank the importance of his/her health issues or medications 44. This process of prioritizing allows advertisers to prioritize theirs advertisements for a particular consumer according to that consumer's priority.

The released clinical data is analyzed by the system and categorized into medication data and clinical healthcare data 45 which represent the consumer's health profile. The medication and clinical healthcare data are then converted into numeric codes 46 retrieved from the MIDT described in FIG. 3. These encoded medication and healthcare data then generate the consumer's assigned consumer targeted profile (CTP) 48. Therefore, each consenting consumer will have an assigned CTP. Theoretically, multiple consenting consumers may have identical CTPs.

The system stores all the assigned CTPs of all the consumers in network and makes them available to the network's advertisers 48 in order to allow advertisers to target their advertisements to certain consumer based on that consumer's CTP. This process allows the advertisers to specifically target the intended audience but does not allow the advertisers to know the specific identity of each targeted audience member which is in accordance to the HIPAA law.

Figure 5:
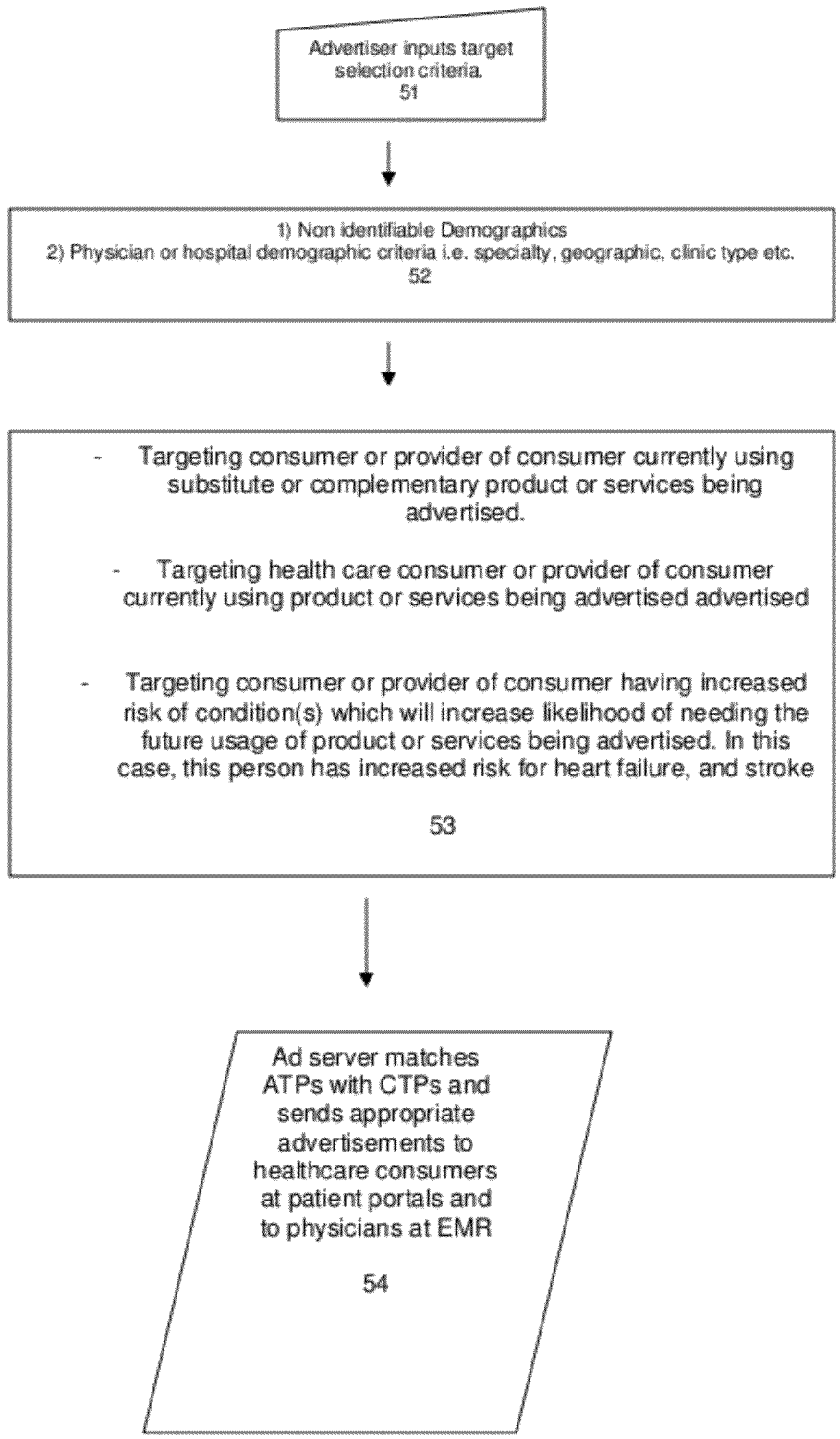
FIG. 5 illustrates how an ATP is generated.

FIG. 5 illustrates the process of creating an advertising targeting profile (ATP) for a particular advertisement. The advertisers first input target criteria 51 which includes information regarding the products that they wish to advertise in the network. The advertisers can then choose to send their advertisements to consumer and healthcare providers based on non-identifiable demographics or physicians/hospital demographics (i.e., physician's specialty, geographic, etc.) 52. If advertisers wish to target a more specific group of consumers and/or providers 53, they may use the MIDT table to specify which group of consumers and/or providers they wish to receive their advertisements. The MIDT table allows advertisers to target many different healthcare consumers and providers including consumers who are currently using their medications, who have the indicated conditions for the product being advertised, who are using complementary products to the product being advertised, who are using a product that is a direct competitor of the product being advertised, and who have associated or risk factors for the condition which his product is approved to use for treatment. Similarly, the MIDT table allow the advertisers to target health care providers who are treating consumers who are currently using their medications, who have the indicated conditions for the product being advertised, who are using complementary products to the product being advertised, who are using a product that is a direct competitor of the product being advertised, and who have associated or risk factors for the condition which his product is approved to use for treatment.

Each advertisement is then assigned an ATP based on the advertiser's above selection. The central ad server matches the advertisements' ATPs with the consumers' CTPs and delivers these advertisements to the appropriate consumers at the patient portal and physicians at the EMR when a match is found 54.

Figure 6:
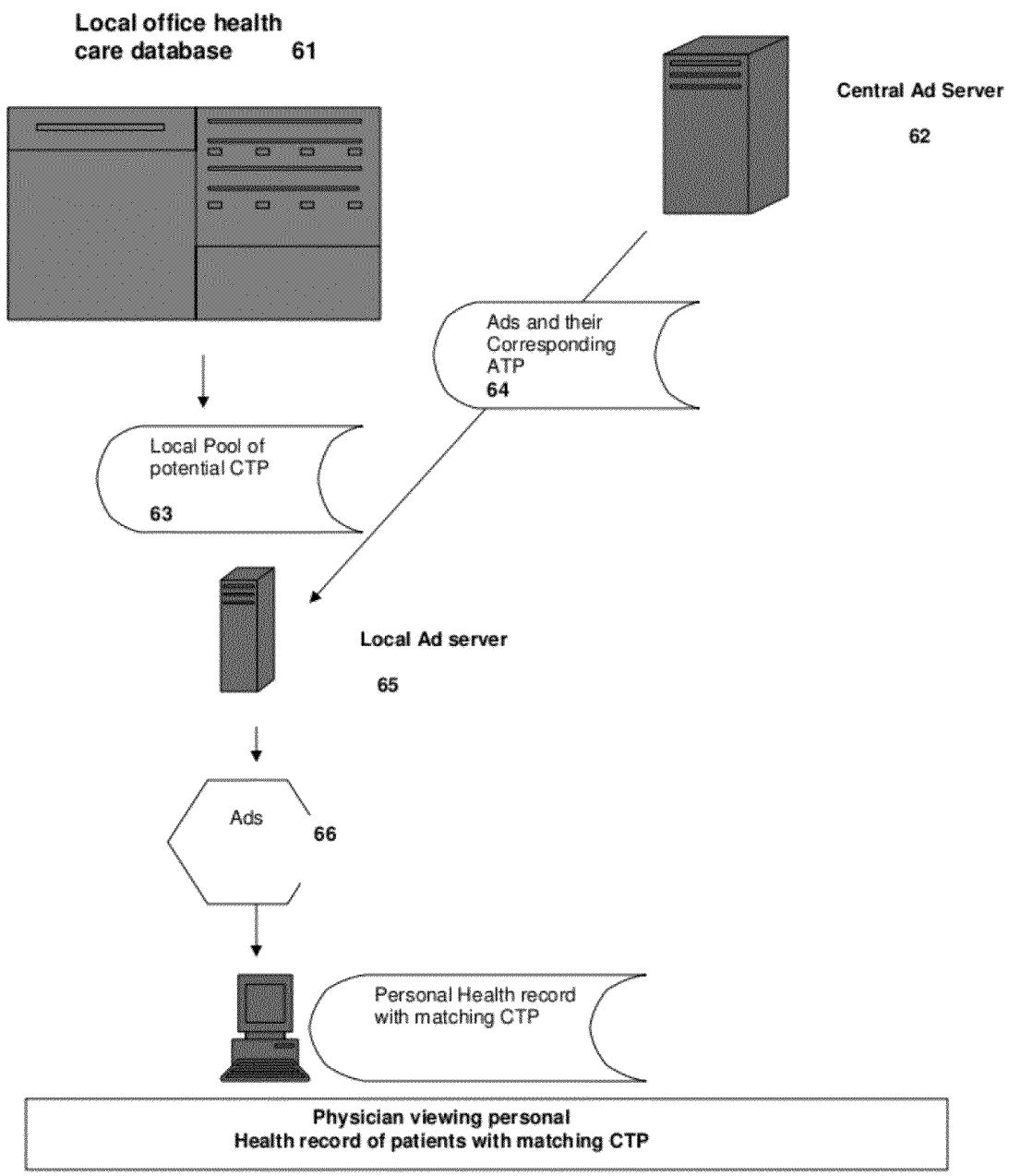
FIG. 6 describes the interaction between the central ad server and the local ad server.

FIG. 6 describes another way that advertisements may be distributed to physicians or healthcare providers. If a physician or healthcare provider houses a local healthcare database at their office 61, a local ad server 65 can be placed at the respective facility or office.

A central ad server 62 sends advertisements and their corresponding APT codes 64 to a local ad server 65. The advertisements are held locally at the local ad server 65, which then matches the ATPs with the available local pool of potential CTPs 63 located in the local healthcare database 61. The local ad server then delivers the appropriate advertisements to the physicians at the EMR according to the ATP/CTP match 66.

Figure 7:
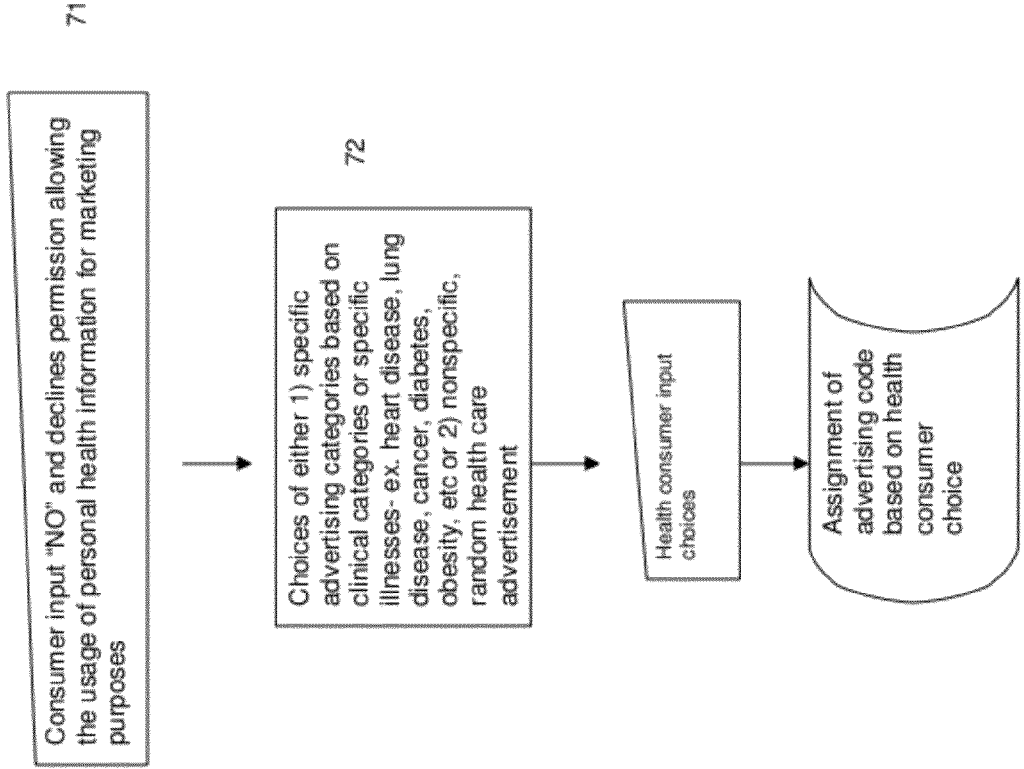
FIG. 7 describes the process of permissive advertising.

FIG. 7 illustrates the process of permissive advertising. When a consumer declines to give his consent to release his medical records for marketing 71, the system then gives the consumer a choice of receiving various advertisements that may be of interest to the consumer 72. The consumer may choose to have certain categories of health advertising to be shown to him directly because of his general interest. For instance, he/she may be asked if he/she is interested in receiving advertisements for products related to heart disease, lung disease, cancer, or other illnesses. If the consumer chooses to view any of these advertisements, then the central ad server delivers such advertisements to the consumer at the patient portal.

If the consumer does not have a preference of what type of advertisements he/she wishes to receive, then the central ad server sends non-specific, random healthcare and non-healthcare advertisements to him/her at the patient portal.

Figure 8:
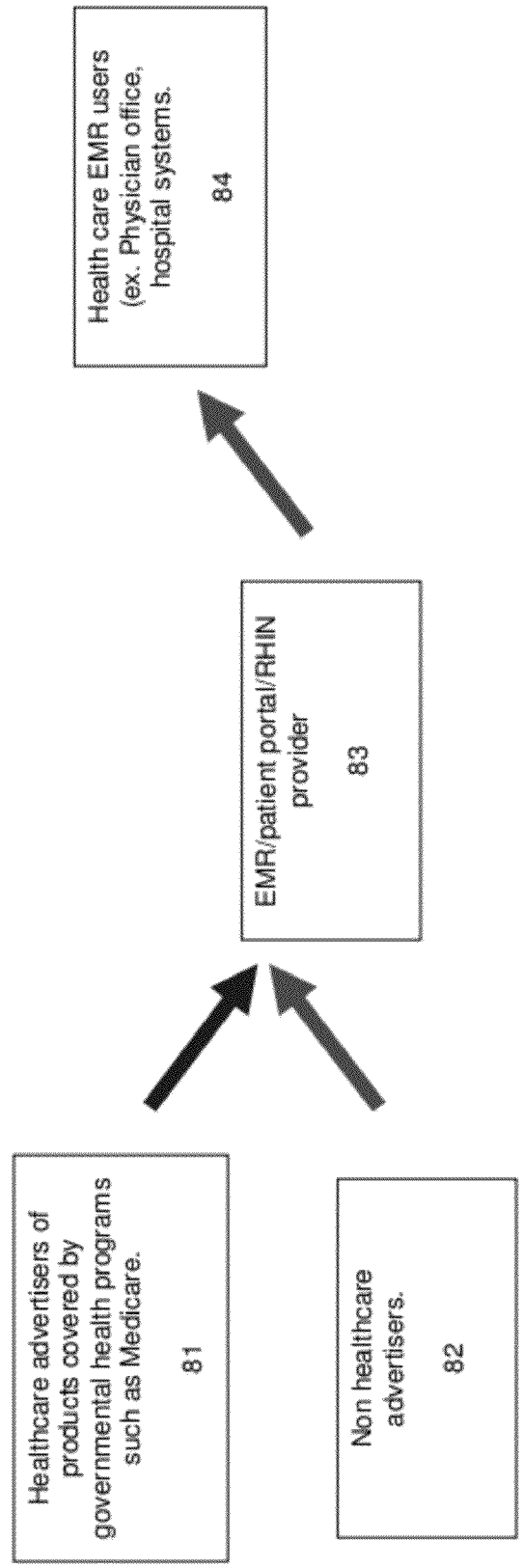
FIG. 8 is a diagram of the revenue distribution model of the present system

FIG. 8 illustrates the revenue distribution model of the present method and system. Revenues generating from healthcare advertisements of products covered by Federal Healthcare Programs such as Medicare 81 are prohibited by anti-kickback laws from flowing to healthcare providers who employ the EMR system. This revenue stays with the EMR, patient portal or RHIN providers 83. Anti-kickback law prevents physicians who are owners of the EMR systems to directly receive revenue from advertisers of pharmaceutical or medical products. Revenues generated from non-healthcare advertisements 82, on the other hand, are not under the jurisdiction of the anti-kickback law, therefore, may be shared with healthcare providers at the EMR 84.

Consequently, the revenue distribution model of the present invention effectively allows EMR users such as physicians at the EMR office to generate revenues from non-healthcare advertisements.

While the invention herein disclosed has been described by means of specific embodiments and applications thereof, other modifications, variations, and arrangements of the present invention may be made in accordance with the above teachings other than as specifically described to practice the invention within the spirit and scope defined by the following claims.

What is claimed:

1. An electronic healthcare advertising system comprising:
a centralized healthcare database;
a web-based patient portal;
a protocol at said web-based patient portal;
an EMR system;
a central ad server;
a local ad server;
a MIDT table;
    a RHIN that bridges said EMR system and said patient portal to create a healthcare network of physicians, healthcare consumers, and other providers;
    an advertiser portal used by an advertiser to upload advertisements onto said central ad server;
    a private secured access point for other healthcare providers;
    wherein said protocol at said patient portal allows said healthcare consumer to choose to give consent to release his health record for marketing purposes, select from a menu of possible advertisement categories to be generated, or choose to receive non-specific advertisements in a manner compliant with HIPPA laws, and then prompts said healthcare consumer to prioritize the different health issues and medications taken from his health record responsive to said consent being given;
    information from said health record is categorized into medication data or clinical health data and is encoded using numeric codes of a MIDT table if said consent is given by said healthcare consumer, said numeric codes are used to generate consumer targeting profiles (CTPs) and advertising targeting profiles (ATPs) and said CTPs and ATPs are matched by said central ad server; said CTPs and said ATPs include indication for product or services, competitive product or services, complementary product or services, or risk factors for illness which will require product or services; and
    said central ad server distributes said advertisements, based on non-identifiable or de-identified health information, and demographics and on multiple targeting profiles created by combining one or more categories encoded using the numeric codes of said MIDT table, to said healthcare provider at said EMR system and said healthcare consumer at said patient portal based on an ATP and CTP match.

2. The system of claim 1, wherein said targeting profiles include consumers with conditions matching a Federal Food and Drug Administration (FDA) approved usage of a product or services being advertised, consumer who are using complementary products or services to a product or services being advertised, consumers who are using a product or services that are a direct competitor of a product or services being advertised, and consumers who have associated illness or risk factors for a condition which a product or services are approved to use for treatment.

3. The system of claim 1, wherein said central ad server prioritizes said advertiser's advertisements according to said healthcare consumer's prioritization.

4. The system of claim 1, wherein said patient portal gives said healthcare consumer the ability to receive health related advertisements from various categories selected by said healthcare consumer if said healthcare consumer declines to give consent to release his health record for marketing purposes.

5. The system of claim 1, wherein said central ad server can send non-specific, random health related or non-health related advertisements to said healthcare consumer at said patient portal if said healthcare consumer does not have a preference for any advertisements from said categories.

6. The system of claim 1, wherein said centralized healthcare database interacts with said EMR system and said patient portal via said RHIN, and holds general medical clinical information collected from said EMR system and said patient portal.

7. The system of claim 1, wherein said EMR system records clinical data of said healthcare consumer by said healthcare provider, and sail clinical data can exist on a local software application at said healthcare provider's location or said centralized healthcare database, or hosted by an application service provider.

8. The system of claim 1, wherein said EMR system and RHIN allow said healthcare provider to communicate with other healthcare providers, health insurers, payers, and other healthcare facilities.

9. The system of claim 1, wherein said EMR system is located at said healthcare provider's location.

10. The system of claim 1, wherein said patient portal allows said healthcare consumer to communicate with said healthcare provider and view personal healthcare records of said healthcare consumer.

11. The system of claim 1, wherein said patient portal allows said healthcare consumer to receive notifications from said healthcare provider's office, request medications and/or refills, and schedule an appointment to visit said healthcare provider.

12. The system of claim 1, wherein said patient portal allows said healthcare consumer to conduct a search for healthcare information.

13. The system of claim 1, wherein an information entered into said patient portal by said healthcare consumer is stored at said centralized healthcare database.

14. The system of claim 13, wherein said information can be shared with said healthcare provider at said EMR system.

15. The system of claim 1, wherein said central ad server can deliver advertisements to said healthcare provider directly to said EMR system or to said local ad server.

16. The system of claim 15, wherein said local ad server is located at said healthcare provider's location.

17. The system of claim 15, wherein said local ad server sends said advertisements to said EMR system.

18. An EMR revenue generating and distribution method comprising:

creating a healthcare network of physicians, healthcare consumers, and other healthcare providers;

enabling a healthcare consumer to consent to releasing his health record for marketing purposes at a patient portal, to select from a menu of possible advertisement categories to be generated, or to choose to receive non-specific advertisements in a manner compliant with HIPPA laws, and then prompts said healthcare consumer to prioritize the different health issues and medications taken from his health record if said consent is given;

uploading an advertisement to a central ad server;

encoding a healthcare consumer's released health record using numeric codes in a MIDT table if consent is given by said healthcare consumer, information from said health record is categorized into medication data or clinical health data;

encoding an advertisement using the numeric codes in said MIDT table;

generating a CTP for said health record using the numeric codes ha said MIDT table;

generating an ATP for said advertisements using the numeric codes in said MIDT table, wherein said CTPs and ATPs are matched by said central ad server; said CTPs and said ATPs include indication for product or services, competitive product or services, complementary product or services, or risk factors for illness which will require product or services; and delivering an advertisement, based on non-identifiable or de-identified health information, and demographics and on multiple targeting profiles created by combining one or more categories encoded using the numeric codes of said MIDT table, to a healthcare provider at an EMR system and healthcare consumer at the patient portal based on an ATP and CTP match; and distributing advertising revenues to healthcare providers who use an EMR system.

19. The method of claim 18, further comprising the steps of matching CTPs with ATPs, prioritizing a healthcare consumer's data on his health record, distributing an advertisement to based on said healthcare consumer's non-identifiable demographics and/or clinical data of said healthcare consumer if consent is given by said healthcare consumer and/or said healthcare provider's demographics, providing said healthcare consumer with the ability to receive health related advertisements in various categories selected by said health care consumer if said health care consumer declines to give said consent to release said health record for marketing purposes, distributing an advertisement based on said CTP and ATP matches, and distributing non-specific, random health related or non-health related advertisements to said healthcare consumer at said patient portal if said healthcare consumer does not have a preference for any advertisements from said categories.

* * * * *